(12) United States Patent
Morrison et al.

(10) Patent No.: US 9,204,904 B2
(45) Date of Patent: Dec. 8, 2015

(54) VARIABLE ANGLE ADAPTIVE PLATE

(75) Inventors: Matthew M. Morrison, Cordova, TN (US); Michael S. Veldman, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1280 days.

(21) Appl. No.: 13/081,732

(22) Filed: Apr. 7, 2011

(65) Prior Publication Data

US 2011/0184461 A1    Jul. 28, 2011

Related U.S. Application Data

(63) Continuation of application No. 11/507,707, filed on Aug. 22, 2006, now Pat. No. 8,002,808, which is a continuation of application No. 10/301,998, filed on Nov. 22, 2002, now Pat. No. 7,094,238.

(51) Int. Cl.
| | |
|---|---|
| *A61B 17/56* | (2006.01) |
| *A61B 17/70* | (2006.01) |
| *A61B 17/88* | (2006.01) |
| *A61B 17/80* | (2006.01) |
| *A61B 17/86* | (2006.01) |
| *A61B 17/02* | (2006.01) |

(52) U.S. Cl.
CPC .......... *A61B 17/7059* (2013.01); *A61B 17/701* (2013.01); *A61B 17/7007* (2013.01); *A61B 17/7058* (2013.01); *A61B 17/8866* (2013.01); *A61B 17/7044* (2013.01); *A61B 17/809* (2013.01); *A61B 17/864* (2013.01); *A61B 2017/0256* (2013.01)

(58) Field of Classification Search
CPC ........................ A61B 17/7059; A61B 17/8042
USPC ...................... 606/280–298, 70, 71
See application file for complete search history.

(56) References Cited

U.S. PATENT DOCUMENTS

| | | |
|---|---|---|
| 2,243,515 A | 5/1941 | Van Sant |
| 5,092,893 A | 3/1992 | Smith |
| 5,108,395 A | 4/1992 | Laurain |
| 5,234,431 A | 8/1993 | Keller |
| 5,261,910 A | 11/1993 | Warden et al. |
| 5,304,179 A | 4/1994 | Wagner |
| 5,324,290 A | 6/1994 | Zdeblick et al. |
| 5,380,326 A | 1/1995 | Lin |
| 5,487,743 A | 1/1996 | Laurain et al. |
| 5,520,688 A | 5/1996 | Lin |

(Continued)

FOREIGN PATENT DOCUMENTS

| | | |
|---|---|---|
| FR | 2 763 828 | 2/1998 |
| FR | 2 758 971 A1 | 8/1998 |

*Primary Examiner* — Mary Hoffman

(57) ABSTRACT

A device for supporting and/or assisting in bone fusion, particularly in the spine, is described. A plate member is provided, along with two or more attachment members that are anchorable to bones. In one embodiment, the plate member has a slot near one end and an aperture at another end. The attachment members include threaded posts for connection to the plate member via the latter's slot(s) and aperture(s). Alternatively, attachment members need not have a threaded post, and attachment members may be connected to the plate member via a bone bolt or similar fixation member. The slot(s) allow a single plate member to be used for a variety of operative situations and anatomies. A device for repositioning bones and a method for using the disclosed devices is also described.

19 Claims, 8 Drawing Sheets

(56) References Cited

U.S. PATENT DOCUMENTS

| | | | |
|---|---|---|---|
| 5,591,167 A | 1/1997 | Laurain et al. | |
| 5,601,553 A | 2/1997 | Trebing et al. | |
| 5,603,713 A | 2/1997 | Aust et al. | |
| 5,613,967 A | 3/1997 | Engelhardt et al. | |
| 5,613,968 A | 3/1997 | Lin | |
| 5,620,443 A | 4/1997 | Gertzbein et al. | |
| 5,693,053 A | 12/1997 | Estes | |
| 5,728,127 A | 3/1998 | Asher et al. | |
| 5,735,853 A | 4/1998 | Olerud | |
| 5,797,912 A | 8/1998 | Runciman et al. | |
| 5,810,823 A | 9/1998 | Klaue et al. | |
| 5,885,286 A | 3/1999 | Sherman et al. | |
| 5,915,902 A | 6/1999 | Patterson et al. | |
| 5,984,924 A | 11/1999 | Asher et al. | |
| 6,066,140 A | 5/2000 | Gertzbein et al. | |
| 6,083,224 A | 7/2000 | Gertzbein et al. | |
| 6,206,882 B1 | 3/2001 | Cohen | |
| 6,214,012 B1 | 4/2001 | Karpman et al. | |
| 6,224,602 B1 * | 5/2001 | Hayes | 606/296 |
| 6,254,603 B1 | 7/2001 | Gertzbein et al. | |
| 6,287,309 B1 | 9/2001 | Baccelli et al. | |
| 6,503,250 B2 * | 1/2003 | Paul | 606/279 |
| 2002/0120273 A1 * | 8/2002 | Needham et al. | 606/61 |
| 2002/0183754 A1 * | 12/2002 | Michelson | 606/70 |
| 2005/0137597 A1 * | 6/2005 | Butler et al. | 606/69 |

* cited by examiner

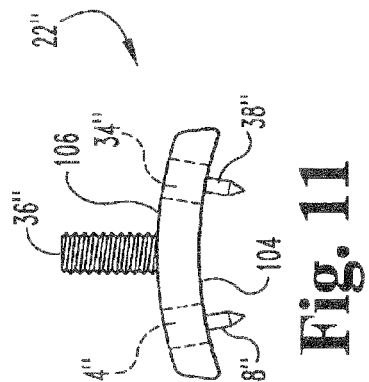
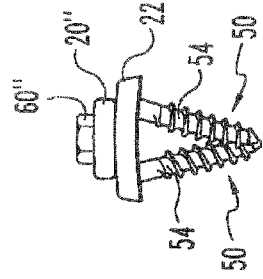
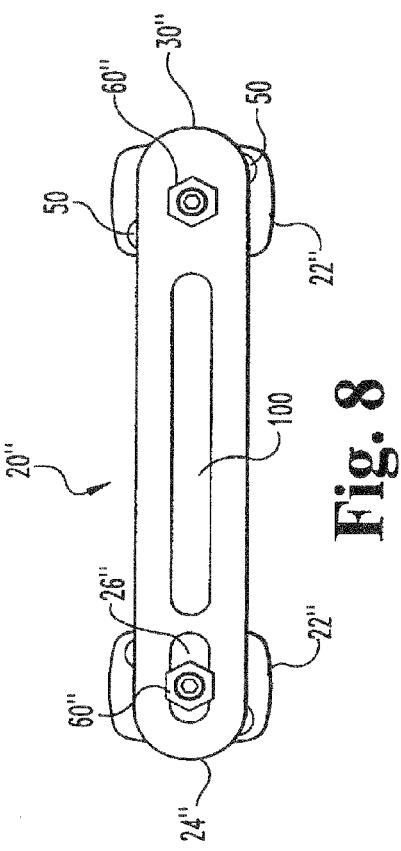
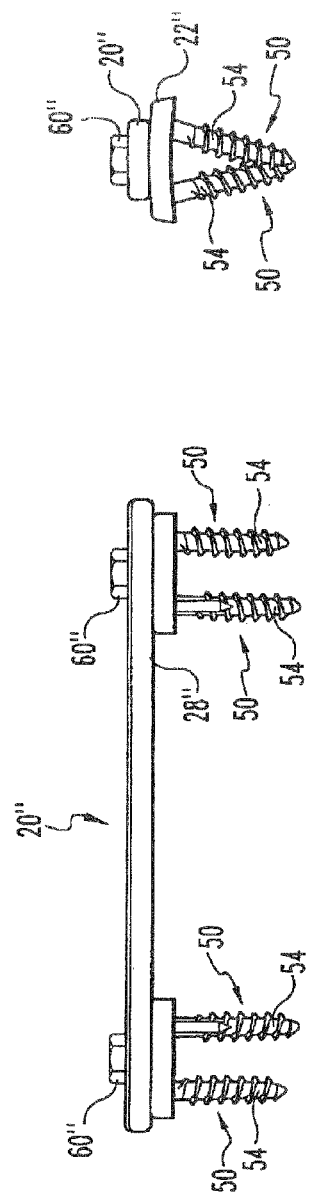

VARIABLE ANGLE ADAPTIVE PLATE

CROSS REFERENCE TO RELATED APPLICATIONS

The present application is a continuation of co-pending U.S. patent application Ser. No. 11/507,707 filed on Aug. 22, 2006, now U.S. Pat. No. 8,002,808, which is a continuation of U.S. patent application Ser. No. 10/301,998 filed on Nov. 22, 2002 and issued as U.S. Pat. No. 7,094,238, the contents of each application hereby incorporated by reference in their entirety.

FIELD OF THE INVENTION

The present invention is generally in the field of orthopedic implants and corrective devices, and specifically concerns plate systems for correcting spinal injuries or abnormalities.

BACKGROUND OF THE INVENTION

Many implant systems are known for correcting orthopedic abnormalities, whether such abnormalities are naturally occurring or are due to disease or injury. For example, in cases of abnormal spinal curvature, such as scoliosis, or in cases in which one or more vertebrae must be repaired or removed, such as in tumor or fracture cases, it is common to implant a device that provides stability and support to the spine.

Two particular types of systems are well known for such repair or therapy. First, rod-based systems are known, in which a rod or bar is fixed to the spine via bone screws or hooks. Generally, the screws or hooks are implanted into one or more spinal segments, the spine is adjusted, and the rod or bar is fixed to the screws or rods to hold the spine in the corrected position. These types of systems are commonly used to correct an abnormal curvature and/or to support weak or injured vertebrae in an approximately normal curvature. One example of such a system is disclosed in U.S. Pat. No. 5,005,652 to Cotrel.

A second type of system for spinal therapy is a plate-based system. In general, a flat plate with one or more slots or holes through it is attached to one or more spinal segments by bone screws or bolts. Such plates are commonly used for the purpose of immobilizing the spinal segment(s) and promoting healing of vertebrae suffering from injury, tumor removal or other trauma or abnormality. Commonly, fusion among the vertebrae in the segment(s) is a desired therapeutic outcome, and plate-based systems are generally suited to promotion of fusion. As an example of such a plate-based system, see U.S. Pat. No. 6,315,779 to Morrison, et al., the entirety of which is incorporated herein by reference.

In some cases, plate-based systems directly attached to a bone may be incorrectly used or placed. For example, a slotted plate member that is fixed to a bone directly via a screw or bolt may fail through widening of the slot if the screw or bolt is over-tightened, or if it is placed on bone(s) in a way that could over-stress the plate. As forces from over-tightening or misplacement are transmitted to the plate, and specifically to the sides of the longitudinal slot through the plate, such forces can cause the sides of the plate to bow outward through repeated stress. The result is that the slot widens, which may allow the attaching bolt or screw head to move with respect to the slot, reducing or eliminating the immobilizing capability of the plate system.

To overcome the possibility for such failure, several different options have been proposed. In U.S. Pat. No. 5,613,967 to Engelhardt, a holding bracket is placed over the plate. As the sides of the plate experience outwardly directed forces, the bracket holds the sides of the plate so that they do not bow. In U.S. Pat. No. 6,315,779 to Morrison et al, a stabilizing member is inserted within the plate. The stabilizing member contacts the bolt or screw that is inserted into a vertebra, rather than the plate contacting the bolt or screw, and the stabilizing member cannot be bowed outward.

Some prior art plate-based systems also suffer from a risk of loosening due to backing out of a screw inserted into a vertebra. If a bone screw backs out, e.g. due to improper insertion or unanticipated stress, a plate member is not securely held in contact with the vertebra(e) so as to provide immobilizing support. Fusion, if not already completed, can be interrupted or counteracted, and injury to the vertebrae or associated tissue is possible. Use of caps or other parts over the heads of bone screws is known to help maintain the screws in their inserted positions and sustain secure contact between vertebrae and a plate. However, such devices add to the number of parts, particularly small parts, that a surgeon must handle in implanting the system.

Accordingly, there remains a need for an improved plate-based system that will address these shortcomings.

SUMMARY OF THE INVENTION

In general, an embodiment of the invention can include a plate member having a first end with a slot and a second end with an aperture that may be round, elongated, or have another shape. A plurality of attachment members are connected to the plate member, each of the attachment members having at least one hole for receiving a portion of a bone anchoring member and each adapted for contact with a vertebra. Posts are connected to two of the attachment members and extend through the plate member's slot and aperture in said plate member respectively. Nuts or other locking caps or devices are provided for the posts for locking together the attachment members and the plate member.

In another embodiment, a plate member is provided having a first end with a slot and a second end with an aperture. An attachment member having at least one hole for receiving a portion of a bone anchoring member and adapted for contact with a vertebra connects to the plate member. A bolt having a lower portion threaded for insertion into a bone and an upper threaded portion is also provided, and the upper portion of the bolt is adapted to be inserted through a hole in the attachment member and the slot in the plate member. A nut threads onto the upper threaded portion of the bolt for locking together the attachment member and plate member.

In another embodiment, a plate member having a first end with a slot, a second end with an aperture, and a second slot, a portion of which is between the first slot and the aperture, is provided. First and second attachment members each having at least one hole therethrough are connected to the plate member proximate to the first slot and the aperture, respectively. First and second screws for attaching the attachment members to a bone via the holes in the attachment members are also provided. The plate member includes at least a portion that covers at least a portion of the first and second screws.

In a further embodiment, a method is provided including attaching a first attachment member having a post and a roughened upper side to a first vertebra, and a second attachment member having a post and a roughened upper side to a second vertebra. A plate member having a slot and an aperture is connected to said attachment members, such that the first attachment member's post extends through the slot and the second attachment member's post extends through the aperture. A repositioning device is connected to the posts of the attachment members, and the repositioning device is operated to perform at least one of distraction of the attachment members, compression of the attachment members, and rotation of at least one of the attachment members. The repositioning device may include first and second rods adapted to connect to the attachment members' posts, a first clamp connected to the first rod and a second clamp connected to the second rod, a bar connected to the clamps and having teeth along at least one edge, and a pinion mechanism having teeth that engage said teeth of said bar connected to the first clamp, so that turning the pinion mechanism causes the first clamp and the first rod to move with respect to the second clamp and the second rod. In certain embodiments of the method, the rods are threaded onto the attachment members' posts. Operation of the repositioning device can be continued until the vertebrae are in a desired relative position, and the plate member can be locked with respect to the attachment members so that the vertebrae are maintained substantially in the desired relative position.

BRIEF DESCRIPTION OF THE DRAWINGS

FIG. 3c is a side view of the embodiment shown in FIG. 3a.

FIG. 3d is a bottom view of the embodiment shown in FIG. 3a.

FIG. 8 is a top view of another embodiment of a plate system incorporating the present invention.

FIG. 9 is a side view of the embodiment shown in FIG. 8.

FIG. 10 is a end view of the embodiment shown in FIG. 8.

FIG. 11 is a side view of an embodiment of an attachment member useful in the plate system shown in FIG. 8.

DESCRIPTION OF THE PREFERRED EMBODIMENT

Figure 1:
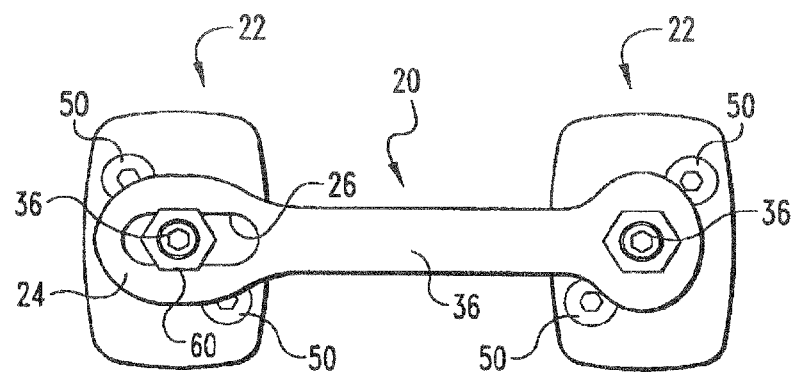
FIG. 1 is a top view of one embodiment of a plate system incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring now to FIG. 1, there is shown a first embodiment of a plate system according to the present invention. In that embodiment, a plate member 20 is connected to attachment members 22. Attachment members 22 are intended to be attached to individual vertebrae, as will be discussed further hereafter. Plate member 20 is to be connected to attachment members 22, so that such individual vertebrae are immobilized with respect to each other.

Figure 2:
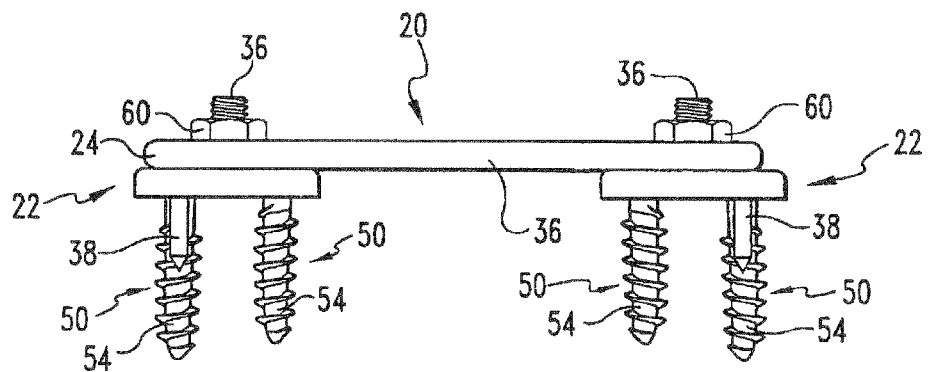
FIG. 2 is a side view of the embodiment shown in FIG. 1.
Figure 3A:
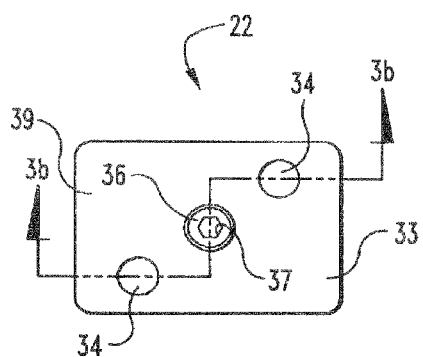
FIG. 3a is a top view of an embodiment of an attachment member useful in the plate system shown in FIG. 1.
Figure 3D:
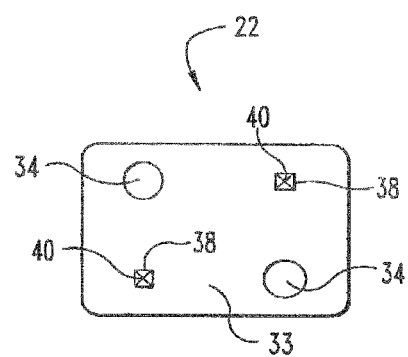
Figure 3B:
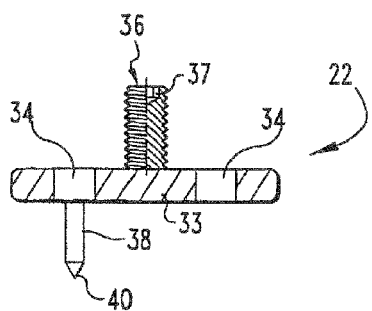
FIG. 3b is a cross-sectional view of the embodiment shown in FIG. 3a along the lines 3b-3b in FIG. 3a, viewed in the direction of the arrows.
Figure 3C:
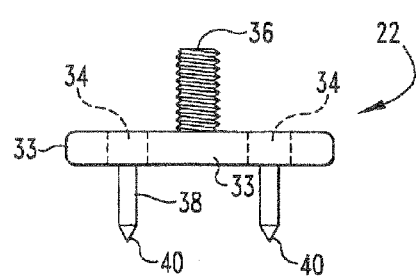
Figure 4:
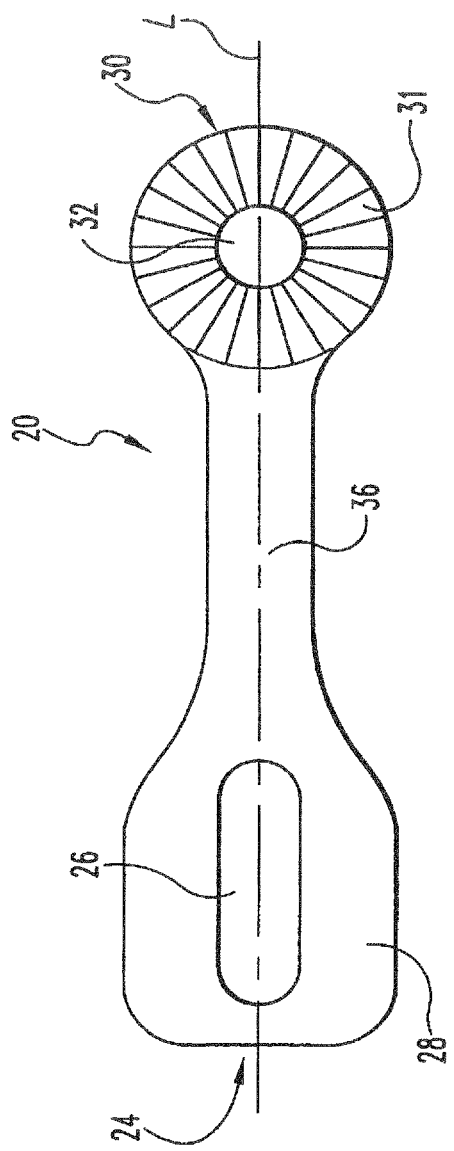
FIG. 4 is a bottom view of an embodiment of a plate member useful in the plate system shown in FIG. 1.

As shown in FIGS. 1, 2 and 4, plate member 20 is a relatively flat, elongated member having a longitudinal axis L. As it is designed for implantation in a living body, it is preferably made of a material compatible with such a use, e.g. titanium, stainless steel, ceramics and/or hard plastics. At a first end 24, plate member 20 includes an elongated slot 26. In a specific embodiment, slot 26 may have a length of from four to ten millimeters. Of course, the length of slot 26 can be increased or decreased depending on the overall size of plate member 20 and/or the size of the post that extends through slot 26 (discussed below). Further, it will be recognized that the length and/or breadth of slot 26, as well as the overall dimensions of plate 20 and others of its features, can be made larger or smaller depending upon the place in the body into which plate member 20 is to be implanted. For example, smaller dimensions may be preferred or required if plate member 20 is to be used in the cervical section of the spine, whereas somewhat larger dimensions may be preferred if plate member 20 is to be used in the thoracic region, or still larger dimensions if used in the lumbar or sacral region of the spine.

End 24 of plate member 20 includes an underside portion 28 that preferably includes a roughened surface, e.g. knurled, grooved, or otherwise, to improve the connection between end 24 of plate member 20 and a corresponding attachment member 22. Knurling of surface 28 is preferred due to relative ease of manufacture while allowing attachment member 22 to connect to end 24 of plate member 20 in a wide range of positions. Plate member 20 has a second end 30 that is opposed to end 24, and has an aperture 32 that extends through plate member 20. In the illustrated embodiment, aperture 32 is a circular hole. It will be understood that aperture 32 can have other shapes, such as a square or other polygonal hole or an elongated slot. End 30 further includes a roughened underside portion 31, which has one or more of the types of roughening described above with respect to underside portion 28 of end 24. In the embodiment shown in FIG. 4, end 30 includes a number of radial splines extending from aperture 32 on underside 31 of plate member 20. Other types of roughening, such as the knurling shown with respect to end 24, could be used instead or in addition to such splines on underside portion 31.

Ends 24 and 30 are generally somewhat wider than middle portion 36 in this embodiment of plate member 20. The wideness of ends 24 and 30 provide additional area to plate member 20 in regions in which plate member 20 is connected to attachment members 22, thus enabling a firmer or stronger connection between plate member 20 and attachment members 22. The narrower middle portion 36 uses less material and enables placement of plate member 20 closer to spinal structures such as spinal processes or pedicles than might otherwise be the case.

Turning now to FIGS. 1, 2 and 3a-3d, there is shown an embodiment of attachment member 22. In that embodiment, attachment member 22 has a generally rectangular base 33 and includes two holes 34 placed in diagonal corners of base 33. However, it will be understood that holes 34 may occupy different locations in attachment member 22. For example, in other embodiments holes 34 may be in the corners along the same side, or amid opposing sides, of attachment member 22. In embodiments in which attachment member 22 has a narrow rectangular base 33 (e.g. where the width of base 33 is not much greater than an appropriate diameter for holes 34), holes 32 may be positioned at or near the ends of base 33 of attachment member 22. In a particular embodiment, holes 34 may include upper surfaces (not shown) that enable countersinking of bone screws. Although two holes 34 are shown in the illustrated embodiments of attachment members 22, it is possible to construct an attachment member 22 (or 22' or 22" as described below) with only one or with more than two holes 34. Post 36 may include a tool-engaging surface, such as internal hexagonal print 37, to assist in moving or turning attachment member 22.

The illustrated embodiment of attachment member 22 includes a post 36, which is externally threaded in one specific embodiment. Post 36 may be made integral with the base portion of attachment member 22. Alternatively, post 36 may be fashioned separately and attached to base 33 of attachment member 22 by welding, threaded engagement, or other known connection techniques. For such alternative cases, an aperture (e.g. a threaded aperture) or other mating area in base portion 33 of attachment member 22 may be provided for post 36. It is preferred that post 36 is attached to the base portion of attachment member 22 prior to use by a surgeon, e.g. during manufacture of attachment member 22, so as to minimize the effort of the surgeon. Past 36 is shown in approximately the center of base portion 33 of attachment member 22, but may be placed in other positions.

Attachment member 22 may also include one or more fixation prongs 38 having a relatively sharp or pointed fixation end 40. Prongs 38 may be made integral with base 33 of attachment member 22, or may be attached to base 33 as described above with respect to post 36. In the illustrated embodiment, prongs 38 are located in diagonal corners of base portion 33 of attachment member 22, e.g., in the corners having holes 34.

As with the bottom surfaces 28 and 31 of plate member 20, in a preferred embodiment a top surface 39 of attachment members 22 is knurled or otherwise roughened. In a specific embodiment, an attachment member 22 designed to connect with end 24 of plate member 20 is knurled on top surface 39 in a similar fashion to the knurling on surface 28 of plate member 20. This will allow such an attachment member 22 to connect to plate member 20 anywhere in the region of slot 26 of plate member 20, and in any orientation. An attachment member 22 designed to connect to end 30 of plate member 20 may include radial splines on top surface 39 extending from post 36 compatible with undersurface 31 of plate member 20. Such splines would allow a secure connection while allowing such an attachment member 22 to rotate with respect to plate member 20. Radial splines are appropriate where an attachment member 22 is to be used with an aperture that does not allow translation of attachment member 22 with respect to plate member 20 (e.g. circular aperture 32). If translation capability between an attachment member 22 and plate member 20 is desired, as with an attachment member 22 proximate to slot 26 of plate member 20, splines may inhibit secure connection in different translational positions of attachment member 22 relative to plate member 20.

Figure 5:
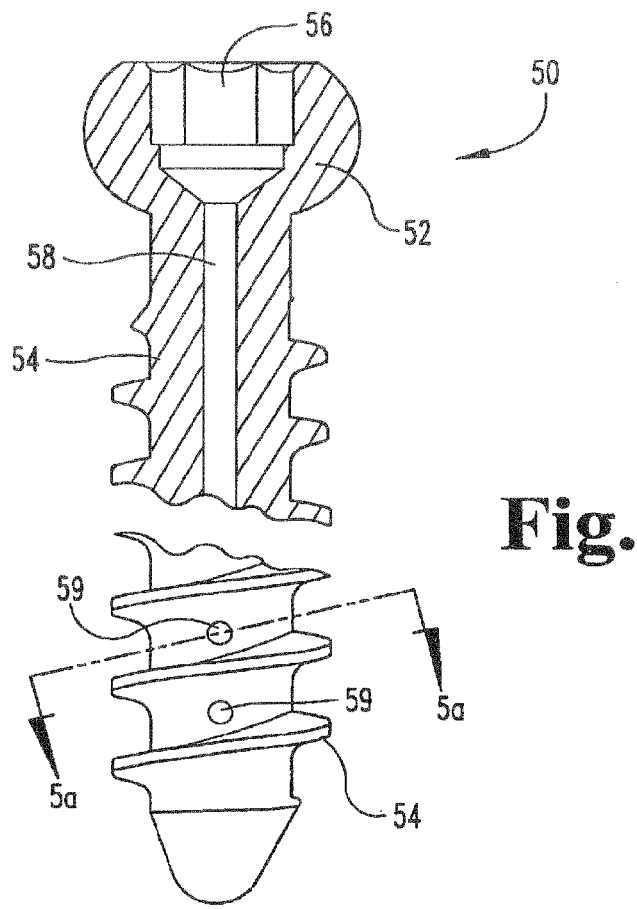
FIG. 5 is a partial cross-sectional view of a screw useful in the plate system shown in FIG. 1.
Figure 5A:
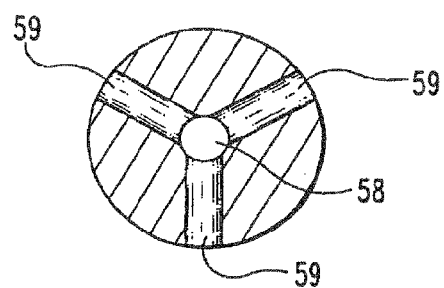
FIG. 5A is a cross-sectional view of the embodiment of the screw shown in FIG. 5 along the lines 5a-5a in FIG. 5, viewed in the direction of the arrows.

There is shown in FIG. 5 a standard bone screw 50 that may be used with attachment member 22. Screw 50 has a head portion 52 and a threaded shaft portion 54, as is known in the art. Head 52 includes an aperture 56 adapted to accept one or more tools useable to insert a screw into a bone. In the illustrated embodiment, aperture 56 includes an internal hexagonal print. Screw 50 may be cannulated, that is, it may have a cannula 58 extending from aperture 56 through the shaft 54 of screw 50. Screw 50 may be a fenestrated screw, i.e. it includes several holes 59 in shaft 54. In an embodiment in which screw 50 is both cannulated and fenestrated, holes 59 can be made to extend from the surface of shaft 54 to the cannula 58. In one particular embodiment, holes 59 are placed 120 degrees apart around the circumference of shaft 54. Holes 59 intersect the surface of shaft 54 at a root of the thread around shaft 54 in the embodiment shown in FIG. 5, but it will be understood that holes 59 could intersect that surface at a thread crest or between a root and a crest. Cannula 58 and/or holes 59 can serve several purposes, including administration of bone growth-inducing substance (e.g. bone morphogenic protein, or BMP), medicinal preparations (e.g. coagulants or antibiotics), or other fluids or substances to be used or placed at the site of implantation. Such substances may be inserted through cannula 58 to holes 59, if both are provided. Cannula 58 and/or holes 59 may also allow bone tissue to grow into screw 50.

A nut 60 is also provided for mating with post 36 of attachment member 22 and locking together attachment member 22 and plate member 20. In the illustrated embodiment, out 60 is shown as a standard hexagonal internally-threaded nut compatible with an embodiment of post 36 having external threads. In another embodiment, nut 60 could be replaced by a nut and washer combination such as that shown in U.S. Pat. No. 6,315,779 to Barker et al., which is incorporated herein by reference. Use of that specific combination would allow multi-axial positioning of attachment member 22 with respect to plate member 20. In yet another embodiment, nut 60 could be a lock nut having a lockable slot, such as that shown in U.S. Pat. No. 5,915,902, which is incorporated herein by reference.

As seen in FIG. 1, when assembled a portion of plate member 20 covers a portion of head 52 of one or more screws 50 that connect attachment members 22 to bone. It will be appreciated that the entire head of one or more screws 50 could be covered by plate member 20. Plate member 20 may contact heads 52 of screws 50 when nuts 60 are tightened to lock plate member 20 and attachment members 22 together, particularly in embodiments hr which holes 34 of attachment members 22 do not allow for countersinking of heads 52.

To use plate member 20, a surgeon makes one or more incisions into a patient, and obtains access to two or more vertebrae defining one or more spinal segments that are to be implanted for stabilization, fusion, or other purposes. Once access is established, the surgeon may prepare the vertebrae by removing bone or adjacent tissue, as is known in the art. Attachment members 22 may then be placed in contact with their respective vertebrae. If one or both attachment members 22 are provided with prongs 38, then such prongs 38 can be partially or completely anchored into the vertebral tissue so as to hold attachment members 22 in place while further procedures are performed. Holes are prepared in the vertebrae corresponding to holes 34 of each attachment member 22. This may be done via a drill or auger placed through holes 34 of attachment member 22, or by other procedures known in the art. The holes in the vertebrae may be tapped. It will be appreciated that these steps may be performed in various orders, e.g. holes in the vertebrae can be drilled prior to introduction of one or more attachment members 22 if the site(s) for placement of attachment member(s) 22 are sufficiently precisely identified. Fixation elements (e.g. screws 50) are then placed through holes 34 of each attachment member 22, and threaded into the holes in the associated vertebrae. Screws 50 are threaded into the vertebral tissue until head portion 52 is securely in contact with attachment member 22 and attachment member 22 is securely fixed between head 52 and the associated vertebra.

Plate member 20 is then placed over attachment members 22. Slot 26 of plate member 20 is placed over post 36 of one attachment member 22. Similarly, hole 32 of plate member 20 is placed over post 36 of the second attachment member 22, so that such threaded post 36 extends through hole 32. Nuts 60 may be threaded or otherwise placed onto one or both posts 36 so that plate member 20 is kept proximate to attachment members 22, but not so tightly that adjustments to the vertebrae and/or to the relative positions of plate member 20 and attachment members 22 cannot be made. The relative distance or position of the vertebrae can be changed so that they form part of a normal spinal curvature and can be fused, or otherwise to treat effectively the existing malformation, injury, or other condition of the given vertebral segment or nearby vertebra(e). During this repositioning, plate member 20 can move with respect to attachment members 22. Specifically, plate member 20 can rotate around the post 36 that extends through hole 32 in plate member 20. Plate member 20 can also translate and rotate with respect to post 36 that extends through slot 26 in plate member 20. Of course, manipulation of the vertebrae can also take place prior to positioning attachment members 22 and/or plate member 20. Consequently, the surgeon can perform distraction, compression, and/or rotation on one or more vertebral segments prior to or while plate member 20 is loosely connected to attachment members 22.

When the vertebral segment is positioned as desired, and attachment members 22 and plate member 20 are connected to the vertebrae as described above, nuts 60 are tightened on posts 36 so as to press together plate member 20 and attachment members 22 and hold them in place relative to each other. In embodiments in which attachment members 22 include knurling or other roughening on an upper side 39, and plate member 20 includes similar knurling or roughening on its underside portions 28 and/or 31, the pressing together of plate member 20 and attachment members 22 will cause these roughened surfaces to interdigitate or otherwise engage, and provide substantially greater security of connection at the interface between plate member 20 and attachment members 22.

Figure 6:
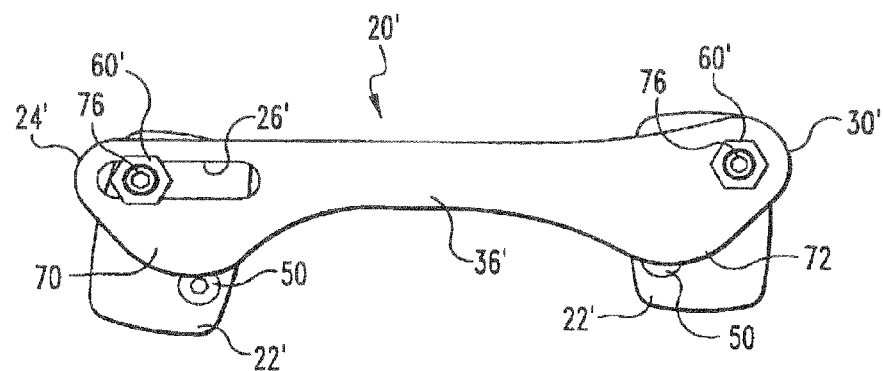
FIG. 6 is a top view of another embodiment of a plate system incorporating the present invention.
Figure 7:
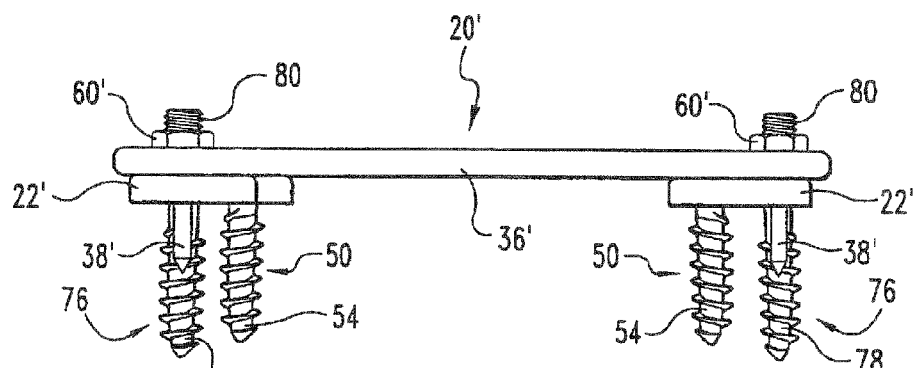
FIG. 7 is a side view of the embodiment shown in FIG. 6.
Figure 13:
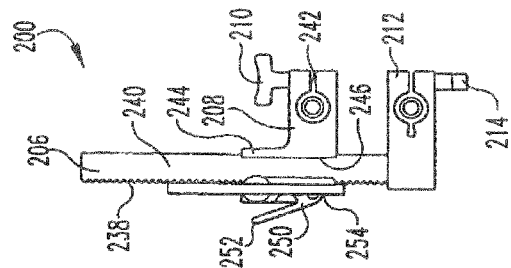
FIG. 13 is a top view of the embodiment shown in FIG. 12.

Referring now to FIGS. 6 and 7, there is shown another embodiment of plate member 20'. Plate member 20' is very similar to plate member 20, and includes a first end 24' having a slot 26', and a second end 30' having a substantially round aperture (not shown) that corresponds to hole 32 of plate member 20. Plate member 20' also preferably includes roughened underside portions corresponding to underside portions 28 and 31 of plate member 20. In the illustrated embodiment, end 24' includes a section 70 that extends laterally with respect to slot 26'. Similarly, end 30' includes a laterally-extending section 72. It will be seen that plate member 20' is in essence a substantially rectangular plate with a slot 26' and a hole (not shown) off the longitudinal center of plate member 20', and with a substantial amount of material removed from at least middle section 36' of plate member 20', so as to conserve material. An alternative embodiment, therefore, could be a rectangular plate member 20' with a slot and a hole off the longitudinal center of the plate member.

Attachment members 22' are substantially the same as attachment members 22, with the exception that attachment members 22' do not include an attached or integral post 36, as attachment members 20 do. In other respects, attachment members 22' are essentially the same as attachment members 20. Thus, attachment members 22' include two holes corresponding to holes 34, and a roughened upper surface that corresponds to surface 39 of attachment members 20. Other features that correspond to features described above are denoted in FIGS. 6 and 7 with a prime (e.g. nut 60' corresponds to previously described nut 60).

In this embodiment, a single screw 50 is used with a given attachment member 22'. Note that sections 70 and 72 of plate member 20' constitute portions of plate member 20' that cover all or a portion of screws 50 anchoring attachment members 22' to bone. In place of a second screw 50 for a given attachment member 22', a bone bolt 76 is provided. Embodiments of bone bolt 76 are described in U.S. Pat. No. 6,315,779 to Barker et al., the entire disclosure of which is incorporated herein by reference. Bolt 76 generally includes a threaded portion 78, a medial head portion (not shown), and a machine threaded upper portion 80. The medial head portion would be larger in diameter than holes 34' of attachment member 22', to anchor members 22' to a bone. The medial head portion can be smaller than the width of slot 26' of plate member 20'.

In use, plate member 20' and attachment members 22' are placed in a manner very similar to that described above with respect to plate member 20 and attachment members 22. Attachment members 22' are placed in contact with respective vertebra, and are affixed to the respective vertebra via a screw 50 through hole 34' in attachment members 22' and into the bone. Bolts 76 are then inserted into holes 34 through attachment members 22' and into the bone. Plate member 20' is placed over the machine threaded portion 80 of bolts 76 and, after any necessary repositioning of the vertebra, nuts 60 are tightened down on machine threaded portions 80 of bolts 76 to lock plate member 20' with attachment members 22' and their respective vertebrae.

A further embodiment is shown in FIGS. 8-11. Features in this embodiment corresponding to features described in connection with previous embodiments are denoted in FIGS. 8-11 by a double prime (e.g. nut 60" corresponds to previously described nut 60). Plate member 20" is substantially rectangular and has a first slot 26" at a first end 24", a second end 30" with a substantially cylindrical aperture (not shown, but corresponds to aperture 32 in plate member 20 described above), and a middle slot 100. As shown in FIG. 10, plate member 20" has an underside with a concave curvature. Like plate member 20, plate member 20" preferably includes roughening on underside portions 28" and 31" in proximity to slot 26" and the aperture near second end 30".

Attachment member 22" is shown in greater detail in FIG. 11. Attachment member 22" is essentially the same as attachment member 22, with the exception that it has an underside 104 that has a concave curvature, and an upper side 106 that has a convex curvature substantially the same as the concave curvature of underside 28" of plate member 20".

As seen in FIG. 10, when assembled a portion of plate member 20" covers a portion of head 52 of one or more screws 50, as further described above with respect to plate member 20.

Plate member 20" can be used to fix or interconnect two or more adjacent vertebrae. If only two vertebrae are to be instrumented, plate member 20" and attachment members 22" are used essentially as described above. Where three or more vertebra are to be instrumented, attachment members 22" are attached to the outermost (i.e. most superior and most inferior) vertebrae essentially as described above. Additionally, attachment members 22, 22', and/or 22" may be attached to one or more of the vertebrae between such outermost vertebrae, and connected to plate member 20" through slot 100, in substantially the manner described above. Bolts (e.g. bolt 76) can be inserted without an attachment member into a vertebra and extend through slot 100 to provide additional stability or correction. It will be observed that other types of implant parts compatible with a slotted plate may also be used with respect to plate member 20" and central slot 100.

Referring now to FIGS. 12-15, there is shown an embodiment of a bone repositioning apparatus 200 for distraction, rotation, holding in place, and/or other manipulation of bones via attachment members 22. Apparatus 200 includes two elongated rods 202, 204 that are connected to a transverse bar 206. In the specific embodiment shown, rod 202 is connected to bar 206 via clamp 208, which is closed by thumb screw 210, while rod 204 is connected to bar 206 via clamp 212 and thumb screw 214. A pinion mechanism 216 may be connected to clamp 212 to interact with bar 206, as further described below.

Figure 15:
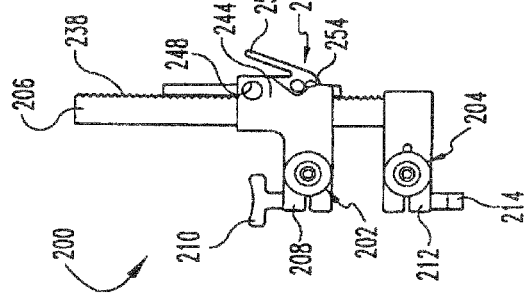
FIG. 15 is a bottom view of the embodiment shown in FIG. 12.
Figure 17:
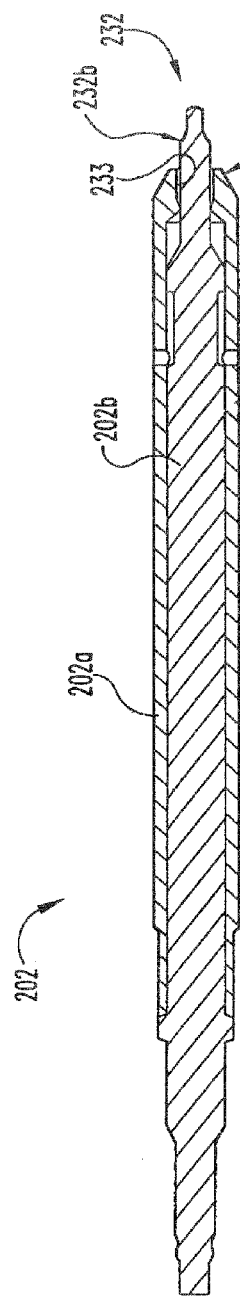
FIG. 17 is a cross-sectional view, taken along the lines 17-17 and viewed in the direction of the arrows, of the embodiment shown in FIG. 16.
Figure 16:
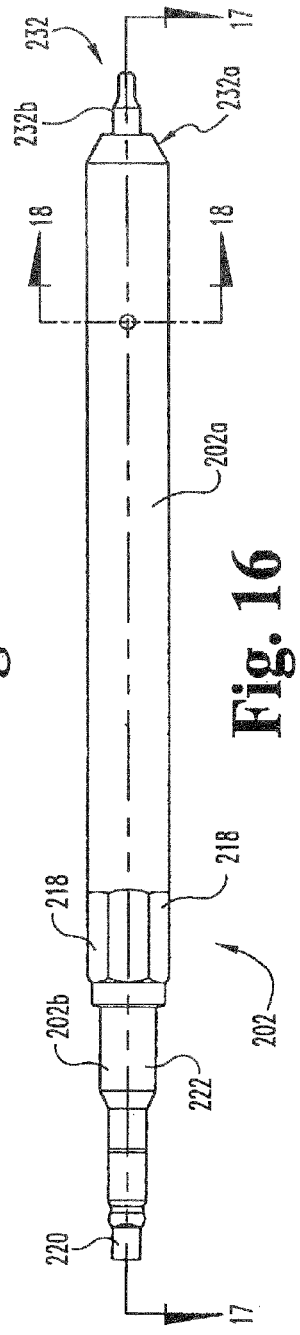
FIG. 16 is a side view of the embodiment of a rod shown with the embodiment of a repositioning apparatus in FIG. 12.
Figure 18:
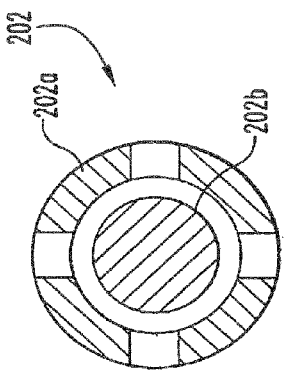
FIG. 18 is a cross-sectional view, taken along the lines 18-18 and viewed in the direction of the arrows, of the embodiment shown in FIG. 16.

Referring now to FIG. 16-18, an embodiment of rod 202 is shown, and it should be understood that the following description is equally applicable to rod 204. In the illustrated embodiment, rod 202 has a generally cylindrical outer sleeve 202a and an inner shaft 202b extending through at least a portion of outer sleeve 202a. Outer sleeve 202a may include flattened portions 218 to assist the surgeon in gripping, turning or otherwise maneuvering sleeve 202a and/or rod 202. Inner shaft 202b may also be generally cylindrical, and may also have flattened portions 220 for gripping, turning or other maneuvering. A connecting portion 222 may be included on or with sleeve 202a and/or shaft 202b for accommodating clamp 208. Connecting portion 222 may simply be a part of the generally cylindrical shaft or sleeve, as shown in FIG. 15, or it may be a cylindrical, annular or other-shaped projection integral with or surrounding at least a portion of the respective sleeve or shaft. In the illustrated embodiment, sleeve 202a is movable translationally and rotationally with respect to shaft 202b. Alternatively, sleeve 202a and shaft 202b may be fixed together or integral with each other.

As shown in FIG. 16, rod 202 has distal end 232 configured to connect to attachment members 22. In one particular embodiment, distal end 232 includes sleeve distal end 232a and shaft distal end 232b. Sleeve distal end 232a may include internal threads 233 for screwing onto the embodiment of post 36 of attachment member 22 that has external threads. Alternatively, or in addition, sleeve distal end 232a may have an end surface roughened for mating with or otherwise configured to connect to a roughened top surface 39 of attachment members 22, or sleeve distal end 232a may have detent mechanism(s), internal prints, or other known structure to connect with, hold to and/or turn post 36 of attachment member 22. Shaft distal end 232b may be provided with an external print such as hexagonal head that can interact with the head of post 36 of attachment member 22.

Bar 206 is shown in one embodiment as a flattened substantially rectangular solid. It will be understood that bar 206 could have any of a number of shapes, such as an elongated solid with a cross-section in the shape of a circle, square, triangle or other polygon. The illustrated embodiment of bar 206 includes a set of teeth 238 along one side, and a scale of numbers can be included along a top surface 240.

Clamp 208 is attached to or integral with bar 206, and in a particular embodiment is a simple C-clamp-type mechanism, with an aperture 242 to accommodate rod 202, sleeve 202a, shaft 202b, and/or connecting portion 222. Tightening thumb screw 210 narrows aperture 242 and clamps rod 202. Clamp 212 has an essentially identical connection to rod 204. Clamp 208 further includes a transverse extension 244, making clamp 204 approximately L-shaped. Extension 244 includes a channel 246 sized to accommodate bar 206 therein. Extension 244 may also have indicator lines for use with a numeric scale, if provided on top surface 240 of bar 206, to gauge the extent of distraction or other manipulation of bones. In a specific embodiment extension 244 also includes a hole 248 communicating with channel 246, and pinion mechanism 216 extends through hole 248. Pinion mechanism 216 thus may contact teeth 238 of bar 206 in rack-and-pinion fashion, so that turning pinion mechanism 216 results in linear movement of clamp 212 with respect to bar 206. A locking pawl 250 may be included. In the illustrated embodiment, pawl 250 is a spring-loaded lever attached to clamp 208, having a pushing surface 252 and a tooth-engaging end 254. Pushing on pushing surface 254 rotates pawl 250 to disengage tooth-engaging end 254 from teeth 238 of bar 206. Releasing pushing surface 254 allows tooth-engaging end 254 to resume its spring-biased position engaging teeth 238. Preferably clamps 208, 212 and bar 206, and pinion mechanism 216 if included, are pre-assembled prior to surgery to form essentially a single "rack" unit for the surgeon's use.

When attachment members 22 are attached to bones, e.g. vertebrae, as described above, compression, distraction, rotation or other maneuvering of the bones can be accomplished via bone repositioning apparatus 200. Rods 202, 204 are inserted into the surgical site and connected to attachment members 22. As noted above, parts of rods 202, 204 (e.g. internal threads 233 of sleeve distal end 232a) connect to rod 36 and/or roughened top surface 39 of attachment members 22. The "rack" unit (pre-assembled bar 206, clamps 208, 212, and pinion mechanism 216) portion can be connected to rods 202, 204 by placing clamps 208, 212 so that a portion of rods 202, 204 respectively extend through apertures 242 of clamps 208, 212. Clamps 208, 212 are then tightened via thumb screws 210, 214. With the parts of the repositioning device 200 assembled and tightened, the surgeon can now apply a distractive or compressive force through the pinion mechanism 216. Turning pinion mechanism 216 in one direction causes the distance between clamps 208, 212 (and rods 202, 204 and their connected bones) to increase, i.e. distraction of vertebrae occurs. Turning pinion mechanism 216 in the other direction, conversely, provides a compression of vertebrae. If present, a scale on surface 240 of bar 206 and indicator lines on clamp 212 enable the surgeon to track the amount of distraction (or compression), and may correspond to a desirable measure such as the size of a graft, intervertebral spacer, plate, or other implant.

Figure 12:
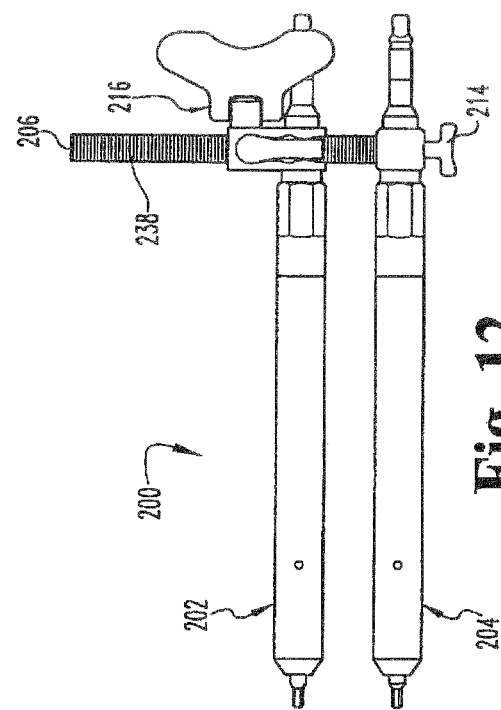
FIG. 12 is a side view of an embodiment of a repositioning apparatus according to the present invention.
Figure 14:
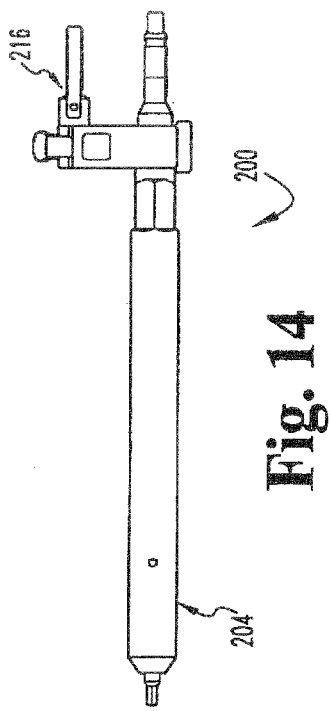
FIG. 14 is an end view of the embodiment shown in FIG. 12.

In the illustrated embodiment, pawl 250 is oriented to allow distraction while pawl 250 is in its spring-biased state (i.e. when tooth-engaging end 254 engages teeth 238), while inhibiting or preventing compression. To enable compression of vertebrae, pawl 250 may be disengaged from teeth 238, or may be oriented 180 degrees opposite to what is shown in FIG. 12, or may be left out of apparatus 200 altogether.

Rotation of a vertebra or other bone is also possible. After rod 202 is connected to an attachment member 22, it will be appreciated that rod 202 (or sleeve 202a or shaft 202b thereof) can be rotated, and such rotation transmitted to the attachment member 22 to which rod 202 is connected and the corresponding bone. A wrench, nut-driver or other tool can be used in connection with flattened portions 218 of outer sleeve 202a and/or flattened portions 220 of inner shaft 202b to turn rod 202. If shaft 202b is movable with respect to sleeve 202a, and shaft 202b includes a connection to attachment member 22 such as the hexagonal print described above, then only shaft 202b need be rotated in order to rotate attachment member 22 and the corresponding bone. Of course, the same process for using rod 204 to rotate a bone can also be used. Further, if rotation is desired after connection of clamps 208, 212 to rods 202, 204, then thumb screws 210, 214 may have to be loosened in order to allow rotation of part or all of rods 202, 204.

Once the surgeon has introduced the desired distraction, compression and/or rotation to a vertebral segment or other bone(s), positioning apparatus 200 can be locked via thumb screws 210, 214 and pawl 250 to preserve the relative positions of rods 202, 204 and their corresponding attachment members 22. With the segment thus held in the desired position, the surgeon can then prepare the bones for further implantation or other treatment. For example, the surgeon can remove tissue from between vertebrae and prepare vertebral surfaces for a cage-type vertebral implant such as that shown in U.S. Pat. No. 5,782,919 to Zdeblick et al. (the entire disclosure of which is hereby incorporated herein by reference), or similar implant or graft.

The positioning apparatus 200 or parts of it can also be used in association with the plate member 20 described above, Vertebrae in one or more vertebral segments are prepared and implanted with attachment members 22 and plate member 20 is placed atop them, as described above. Nuts 60 are threaded onto rods 36 of attachment member as described above, but are not tightened. Positioning apparatus 200 is then introduced and connected to attachment members 22. For example, rod 202 (including sleeve 202a and shaft 202b, each of which are movable with respect to each other) is connected to an attachment member 22 so that sleeve distal end 232a is adjacent to or abuts plate member 20 and nut 60 (for example by threading onto post 36), and shaft distal end 232b connects with post 36 of attachment member 22 (for example via an external print compatible with internal print 37 of post 36). Rod 204 may similarly be connected to the second attachment member 22. The remaining parts of the embodiment of positioning apparatus 200 described above are used as previously disclosed.

The surgeon then introduces the desired compression, distraction and/or rotation via positioning apparatus 200. During such procedure(s), one or both attachment members 22 may change position with respect to plate member 20. When manipulation of attachment members 22 and their corresponding vertebrae is complete, positioning apparatus 200 is locked to preserve their relative positions. Nut 60 can then be tightened with a wrench placed below sleeve 202a. If sleeve 202a is provided with an internal print at distal end 232a corresponding to nut 60, in addition to or instead of threads 233, sleeve 202a can be rotated to tighten nut 60 down onto plate member 20, thereby locking plate member 20 to attachment member 22, and holding the corresponding vertebrae in the desired relative position.

The preceding discussion has principally concerned the embodiment of attachment member 22 that includes a rod 36. As noted previously, rods 202, 204 can include roughening at a distal end (e.g. distal end 232a of sleeve 202a) that mates or otherwise connects with roughened upper surface 39 of attachment member 22. Thus, even if the embodiment of attachment member 22 not having a rod is used, positioning apparatus 200 can be used.

All parts described herein should be manufactured of titanium, stainless steel, certain ceramics or hard plastics, or other material that are biocompatible and are sufficiently sturdy to support human or animal bone structures, and particularly the spine. It will be further be observed that although certain screws and bolts have been described above, that other types of bolts, screws, or other fixation members may be used in connection with the present invention.

It will be appreciated that the above embodiments can be constructed for use in the sacral, lumbar, thoracic and/or cervical regions of the spine, and for use along the junctions of those regions. The size of a given embodiment will depend on the region in which it is used. It is also contemplated that embodiments can be used in connection with other bony structures.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, out 60 is provided as the locking mechanism for use with a threaded post 36. Other types of posts and locking mechanisms could be used, such as a post that includes grooves, holes or ridges and a lock that has sufficiently strong ratchet, pawl, spring or detent-type holding structure. As another example, although plate members 20, 20' and 20" are described and shown with a longitudinal slot at one end and a circular aperture at the other, it is possible for the plate member to have a slot at each end, or for a slot to have a non-zero angle with respect to a longitudinal axis of the plate member. As still a further example, any embodiment of a plate member may have roughening on its entire underside, and may have a concave underside. In yet a further example, rods 202, 204 of repositioning apparatus 200 may be internally configured to allow nut 60 to placed on post 36 after repositioning occurs. For instance, sleeve 202a may be internally hollow and hexagonal shaped to accommodate nut 60, and shaft 202b may be smaller than the hole through nut 60 and have an external print or other structure to hold post 36. Once shaft 202b holds post 36, nut 60 can be inserted around shaft 202b and within sleeve 202a, so that nut 60 slides down and onto post 36. Rotation of sleeve 202a then tightens nut 60 onto post 36.

What is claimed is:

1. An apparatus, comprising:
a plate having a first end, a second end, an upper surface, an opposite lower surface, a perimeter, a first aperture extending through said plate proximate said first end, and a second aperture extending through said plate proximate said second end;
an attachment member having a top surface, an opposite bottom surface and spaced apart first and second holes extending therethrough from said top surface to said bottom surface, said attachment member adapted for anchoring to a vertebra and to connect to said plate proximate one of said first and second apertures; and
first and second screws each having a shaft and a head portion at one end of said shaft for anchoring said attachment member to bone, at least a portion of said head portion of said first screw being positioned in said first hole and at least a portion of said head portion of said second screw being positioned in said second hole;

wherein at least a portion of said perimeter of said plate covers at least a portion of each of said head portions with said lower surface of said plate positioned in contact with said top surface of said attachment member and with said head portions at least partially positioned between said plate and said attachment member, and wherein said attachment member comprises a first prong extending from said bottom base positioned at a first corner of said attachment member and a second prong extending from said bottom base positioned at an opposite second corner of said attachment member, said first and second prongs each including a pointed distal fixation end.

2. The apparatus of claim 1, further comprising:
a second attachment member having a top surface, an opposite bottom surface and at least one hole extending therethrough from said top surface to said bottom surface, said second attachment member adapted for anchoring to a second vertebra and to connect to said plate proximate the other of said first and second apertures; and
a third screw for anchoring said second attachment member to bone with at least a portion of said third screw positioned in said at least one hole of said second attachment member; and
wherein at least a portion of said perimeter of said plate covers at least a portion of said third screw when said second attachment member and said plate are connected.

3. The apparatus of claim 2, wherein one of said first and second apertures comprises an elongate slot.

4. The apparatus of claim 1, further comprising:
a first post connected to a first of said attachment member and extending through said first aperture in said plate, and a second post connected to a second of said attachment member and extending through said second aperture in said plate; and
a first locking means for mating with said first post and locking together said attachment member connected to said first post and said plate, and a second locking means for mating with said second post and locking together said attachment member connected to said second post and said plate.

5. The apparatus of claim 4, wherein one of said first and second apertures comprises an elongate slot.

6. The apparatus of claim 4, wherein said first post extends from said top surface of said first attachment member, and wherein said second post extends from said top surface of said second attachment member.

7. The apparatus of claim 1, wherein said first aperture comprises an elongate slot.

8. The apparatus of claim 7, wherein said second aperture is circular.

9. The apparatus of claim 1, wherein said top surface of said attachment member is roughened.

10. The apparatus of claim 9, wherein said lower surface of said plate is roughened in an area proximate to one of said first and second apertures; and
wherein said roughened area on said top surface of said attachment member is engaged in contact with said roughened area on said lower surface of said plate.

11. The apparatus of claim 10, wherein said roughened area on said lower surface of said plate and said roughened area on said top surface said attachment member each comprises a series of radially extending splines.

12. The apparatus of claim 1, further comprising:
a bolt having a lower portion including threads adapted for anchoring in bone, and an upper portion having threads, said upper portion positioned through said at least one hole of said attachment member and through a corresponding one of said first and second apertures of said plate; and
a nut threaded onto said upper threaded portion of said bolt to lock said attachment member to said plate.

13. The apparatus of claim 12, further comprising:
a second bolt having a lower portion including threads adapted for anchoring in bone, and an upper portion having threads, said upper portion of said second bolt positioned through at least one hole defined by a second of said attachment member and through the other of said first and second apertures of said plate; and
a second nut threaded onto said upper threaded portion of said second bolt to lock said second attachment member to said plate.

14. The apparatus of claim 1, wherein said head portions of said screws are at least partially positioned between said lower surface of said plate and said bottom surface of said attachment member.

15. The apparatus of claim 1, wherein said attachment member includes a base that has a substantially symmetric configuration about each of two orthogonal axes arranged perpendicular to one another.

16. The apparatus of claim 1, wherein said first hole is positioned at a first corner of said attachment member and said second hole is positioned at an opposite second corner of said attachment member.

17. The apparatus of claim 1, wherein said perimeter does not cover at least a portion of said first screw or at least a second portion of said second screw.

18. An apparatus, comprising:
a plate having a first end, a second end, an upper surface, an opposite lower surface, a perimeter, a first aperture extending through said plate proximate said first end, and a second aperture extending through said plate proximate said second end;
an attachment member having a top surface, an opposite bottom surface and spaced apart first and second holes extending therethrough from said top surface to said bottom surface, said attachment member adapted for anchoring to a vertebra and to connect to said plate proximate one of said first and second apertures;
first and second screws each having a shaft and a head portion at one end of said shaft for anchoring said attachment member to bone, at least a portion of said head portion of said first screw being positioned in said first hole and at least a portion of said head portion of said second screw being positioned in said second hole;
a first post connected to a first of said attachment member and extending through said first aperture in said plate, and a second post connected to a second of said attachment member and extending through said second aperture in said plate; and
a first locking means for mating with said first post and locking together said attachment member connected to said first post and said plate, and a second locking means for mating with said second post and locking together said attachment member connected to said second post and said plate,
wherein at least a portion of said perimeter of said plate covers at least a portion of each of said head portions with said lower surface of said plate positioned in contact with said top surface of said attachment member and with said head portions at least partially positioned between said plate and said attachment member.

19. An apparatus, comprising:

a plate having a first end, a second end, an upper surface, an opposite lower surface, a perimeter, a first aperture extending through said plate proximate said first end, and a second aperture extending through said plate proximate said second end;

an attachment member having a top surface, an opposite bottom surface and spaced apart first and second holes extending therethrough from said top surface to said bottom surface, said attachment member adapted for anchoring to a vertebra and to connect to said plate proximate one of said first and second apertures;

first and second screws each having a shaft and a head portion at one end of said shaft for anchoring said attachment member to bone, at least a portion of said head portion of said first screw being positioned in said first hole and at least a portion of said head portion of said second screw being positioned in said second hole;

a bolt having a lower portion including threads adapted for anchoring in bone, and an upper portion having threads, said upper portion positioned through said at least one hole of said attachment member and through a corresponding one of said first and second apertures of said plate; and a nut threaded onto said upper threaded portion of said bolt to lock said attachment member to said plate, wherein at least a portion of said perimeter of said plate covers at least a portion of each of said head portions with said lower surface of said plate positioned in contact with said top surface of said attachment member and with said head portions at least partially positioned between said plate and said attachment member.

* * * * *